United States Patent [19]
Lauer et al.

[11] Patent Number: 5,714,046
[45] Date of Patent: Feb. 3, 1998

[54] SENSOR ELECTRODE FOR USE IN ELECTROCHEMICAL GAS SENSORS

[75] Inventors: Jay M. Lauer; Naim Akmal, both of Hacienda Heights, Calif.

[73] Assignee: Teledyne Industries, Inc., Los Angeles, Calif.

[21] Appl. No.: 868,048

[22] Filed: Jun. 3, 1997

Related U.S. Application Data

[63] Continuation of Ser. No. 567,964, Dec. 6, 1995, abandoned.

[51] Int. Cl.$^6$ .................................................. G25B 11/00
[52] U.S. Cl. ...................... 204/290 R; 204/431; 204/432
[58] Field of Search ............................ 204/290 R, 431, 204/432, 415

[56] References Cited

U.S. PATENT DOCUMENTS

| | | | |
|---|---|---|---|
| 3,429,796 | 2/1969 | Lauer | 204/195 |
| 3,767,552 | 10/1973 | Lauer | 204/195 P |
| 4,077,861 | 3/1978 | Lauer | 204/195 P |
| 4,477,316 | 10/1984 | Sakai et al. | 204/290 R |

OTHER PUBLICATIONS

ASTM Standard Practise for Cleaning Metal prior to Electroplating, Designation B 322–68, 1979, pp. 151–161.
ASTM Standard Specification for Electrodeposited Coatings of Rhodium for Engineering Use, Designation B634–78, May 1978, pp. 504–506.
ASTM Standard Practise for Preparation of Copper and Copper–Base Alloys for Electroplating & Conversion Coatings pp. 110–113, Nov. 1982.
ASTM Standard Guide for Autocatalytic Nickel Deposition on Metals for Engineering Use, pp. 528–535, May 1979.
ASTM Standard Practise for Preparation of Nickel for electroplating with Nickel, pp. 175–177, Apr. 1979.

*Primary Examiner*—Bruce F. Bell
*Attorney, Agent, or Firm*—Edward J. DaRin

[57] ABSTRACT

A sensing surface for a sensing cathode electrode useful in electrochemical gas sensors for sensing active gases in a gas mixture. The gas sensors are utilized in sensing oxygen or exhaust gases from a motor vehicle, so that there is a potential for causing deposits on the sensing surface of the electrode of either lead oxide species or lead carbonate thereon. The sensing surface is plated with rhodium or platinum for rejecting or prolonging the formation of any of the deposits thereon leading to an increase in rated life for the gas sensor greater than heretofore thought possible.

13 Claims, No Drawings

SENSOR ELECTRODE FOR USE IN ELECTROCHEMICAL GAS SENSORS

This application is a File Wrapper Continuation of Ser. No. 08/567,964, filed Dec. 6, 1995, now abandoned.

FIELD OF INVENTION

This invention relates to electrochemical gas sensors for electrically signalling the concentration of an electrochemically active gas in a gas mixture and more particularly to improvements in a sensing surface for the cathode sensing electrode for such gas sensors.

BACKGROUND OF INVENTION

Electrochemical gas sensors are well known in the art and are exemplified by U.S. Pat. Nos. 3,429,796; 3,767,552 and 4,077,861. These prior art gas sensors are utilized for determining the oxygen concentration in a gas mixture in the parts per million through 100%. These oxygen sensor cells typically use a metallic anode electrode immersed in a liquid electrolyte with the gas sensing cathode electrode. The common gas sensor has a lead anode electrode and the electrolyte is an aqueous solution of potassium hydroxide, whereby the electrolyte can contain soluble species of lead, such as lead ion complex, that may be deposited on the sensing surface of the gas sensing electrode. When there is deposition of the lead species on the cathode sensing surface, the cathode sensing portion of the sensing cathode that is covered by the deposit is no longer available for sensing oxygen and the output current of the sensing cell drops in proportion to the area of the cathode covered by the deposit and this deposition of the lead oxide, PbO, may cause the inability to calibrate the sensor resulting in an undesirable shortened life for the sensor. A second type of deposit on the sensing electrode can occur when the gas mixture exposed to the sensing cathode electrode, utilized with a lead anode electrode in an electrolyte of an aqueous solution of potassium hydroxide, contains carbon dioxide thereby creating the potential to deposit lead carbonate on the surface of the sensing electrode resulting, again, in less than rated performance.

In the first described example of the deposition of lead oxide on the sensing electrode that is used to sense various levels of oxygen over time, as the sensor ages the electrolyte becomes saturated with soluble lead ion complex. At this point in the life of the sensor, the lead oxide will deposit or precipitate and normally the deposition occurs on the anode electrode. The sensor continues to age until all of the available lead of the anode electrode is converted to lead oxide, at which point the sensor is considered spent and must be discarded and replaced. Ideally, over the life of the sensor, the lead oxide will have deposited entirely on the anode electrode or other irrevalant surfaces and not the sensing surface of the cathode electrode. The lead oxide, however, does deposit on the sensing surface of the cathode electrode. It has been found that the physical condition of the sensing surface of the cathode electrode in terms of surface smoothness, cleanliness, organic and inorganic inclusions and the type of sensing of metal plated on the electrode can all affect whether or not the deposition occurs.

The second type of cathode deposition may occur when the sensor is utilized for monitoring the exhaust gases from a motor vehicle, in the presence of a lead anode electrode and an solution of potassium hydroxide. In the monitoring of the vehicle exhaust; it is required that the sensor output reading drop from 21% of oxygen in air to 0.1%, within 30 seconds. The sensor can be left in this exhaust mixture containing 10–20% carbon dioxide for 5–20 minutes and can be used to analyze the exhaust gases of up to 15–20 motor vehicles per day. As long as the sensor is left in air between analysis of exhaust mixtures an equivalent amount of time to the time it was exposed to the vehicle exhaust, no problem is normally experienced. However, if the sensor is continuously in a gas mixture of 16% carbon dioxide gas with the balance being nitrogen gas, a mixture which is typically a good laboratory mixture to simulate an automobile exhaust "zero" gas (i.e. having no oxygen), the output reading of the thus exposed sensor will drop to 0.2–0.5% oxygen, stay there, for 60–90 minutes then begin to rise. The applicants have determined that the time that the sensor output reading starts to rise, the rate of that rise, and the level to which the reading rises, depend to a very significant degree on the physical condition of the sensing surface of the cathode electrode as pointed out hereinabove.

When a sensor is exposed to zero gas containing carbon dioxide, it is thought that what occurs is due to the strong basic nature of the electrolyte, the carbon dioxide gas is drawn into the electrolyte thus creating the potential for depositing lead carbonate onto the sensing suface of the cathode electrode. If the cathode surface has appropriate depositing sites, the deposit forms and the lead carbonate is reduced (at least in part), resulting in increased readings of oxygen.

In the prior art sensors various types of gold and silver plating baths have been used to plate the outer surface of cathode electrodes constructed as described in the above referenced prior art patents. A gold plated electrode has been found to produce some lead oxide deposition on the cathode electrode surface during the lifetime of the sensor and causes the sensor output readings to drop in proportion to the amount of the cathode surface area that is covered by this undesirable deposition. This deposition can, in some instances, cause the premature failure of the sensor dropping the sensitivity until the sensor can no longer be calibrated. Silver plated cathode electrodes have not been found to have this type of undesirable deposition. Both silver and gold plated cathode electrodes have been found to have the above described lead carbonate depositions.

When considering the selection of metals available for plating on a cathode electrode surface, the metal selected for use must be inert in the electrochemical sensing arrangement described hereinabove. These inert metals are silver, gold, platinum, iridium, palladium and rhodium. In the past, gold has been most extensively used with silver the second most metal plated on a cathode sensing electrode. The platinum group of metals have been avoided due to their expense, availability and their production of undesirable catalytic effects. With this understanding, tests have been conducted to determine if one or more of the metals discussed hereinabove would give improved performance in rejecting both of the above described undesirable cathode electrode depositions since there is a present need for a cathode electrode plated with an inert metal for use in the above type of sensors that rejects the deposition of lead oxide and lead carbonate onto the sensing surface of a cathode electrode or minimizes the undesirable effects of such deposits leading to the rated life of the sensing cell or greater.

SUMMARY OF INVENTION

The present invention provides an improved sensing surface for a cathode electrode utilized in an electrochemical gas sensor that rejects the deposition of lead oxide deposits thereon and lead carbonate deposits thereon. The electrochemical gas sensor utilizing the improved cathode electrode is included in an electrolyte consisting of an aqueous solution of potassium hydroxide and a lead anode electrode. The electrochemical gas sensor is utilized for measuring or sensing the levels of oxygen in gas mixtures applied thereto and gas mixtures in the form of motor vehicle exhaust gases including carbon dioxide. The improved sensing surface for cathode electrode is a thin layer of rhodium and increased performance is achieved by preparing the electrode substrate to be plated to achieve a smooth surface to accept a thin film of rhodium to be plated thereon. Although rhodium is the presently preferred metal to be plated due to its availability, platinum has been found to have the best long term performance in zero gas.

DETAILED DESCRIPTION OF THE PREFERRED EMBODIMENT OR EMBODIMENTS OF THE INVENTION

Despite the known problems of some of the above inert metals, noted hereinabove, tests were conducted to determine how selected metals or combination of the metals performed and evaluated to determine their performance as to the cathode deposition of lead oxide and under automobile exhaust zero gas conditions. The inert metals plated on a cathode substrate were silver, two types of gold, palladium, platinum, and rhodium. Table I records the test results.

TABLE 1

The numbers under the columns High, Low and Typical/Average in the table represent the number of hours that the referenced metal stayed below the desired 0.1% oxygen in a zero gas consisting of 16% carbon dioxide with the balance of the gas being nitrogen, (16% $CO_2$ balance $N_2$). The numbers represented in paranthesis, ( ), are the referenced metal (s) plated thickness in microinches. The code, illustrated represents the fact of a deposit of lead oxide, PbO, on the cathode electrode surface in terms of the percentage, %, of the area of the deposit on the cathode surface. The coverage symbols ++++ represent the fact that 90-100% of the cathode surface is covered; +++ represents a 70-80% coverage; ++ represents 30-60% of the cathode surface is covered by a deposit; and + represents 10-30% of cathode is a deposit coverage, while a zero, 0, represents the fact no deposit was found.

| | | No. of Cells | High (Hours) | Low (Hours) | Typical/ average (Hours) | PbO Deposits |
|---|---|---|---|---|---|---|
| (1) | Silver(500), | 6 | >10 | 1 | 1.5 | 0 |
| (2) | Silver/Gold, 99.5% pure (500/50) | 3 | 4 | 2 | 3 | ++ |
| (3) | Silver/Gold, 99.5% pure (500/50) | 3 | 7 | 4 | 5 | ++ |
| (4) | Silver/Gold, 99.99% pure (500,1.5) | 3 | >14 | >14 | >14 | ++++ |
| (5) | Gold, 99.99% pure(20) | 3 | 2 | 0.7 | 1.5 | ++ |
| (6) | Silver/ Palladium (500/1.5) | 3 | 3 | 2.5 | 2.5 | ++++ |
| (7) | Platinum(20) | 3 | 210 | 71 | 162 | 0 |
| (8) | Silver/ Rhodium (500/1.5) | 3 | >22 | 16 | 20 | 0 |
| (9) | Rhodium(20), smoothest surface | 9 | 94 | 37 | 60 | 0 |
| (10) | Rhodium(20), 2nd smoothest surface | 3 | 42 | 38 | 40 | 0 |
| (11) | Rhodium (20),slightly rough surface | 6 | >10 | 3 | 4 | 0 |
| (12) | Rhodium(20), new production bath, smooth | 3 | 165 | 22 | 110 | 0 |

In examining the above Table, it will be noted that the silver plated cathode surface, item 1 in the Table, did not have any lead oxide, PbO column, deposits but did not perform well in prolonged exposure to carbon dioxide contained in zero gas. The pure gold plated cathodes, item 5 of the Table, performed fair in zero gas but deposits of PbO covered 30-60% of the sensing surface; a thin layer of pure gold of 1.5 microinches deposited over silver, item 4 illustrated, produced good results in zero gas, but was one of the worst surfaces as to the lead oxide deposits; (++++). The other combinations of silver and gold surfaces, items 2 and 3, produced fair results for the deposit of lead oxide thereon, but only 1-5 hours of below 0.1% results in zero gas. The combination No. 6 of silver and palladium resulted in a worst case of lead oxide deposits or 90-100% coverage of the sensing surface and about the same results as gold, item 5, in response to zero gas. Platinum and Rhodium plated surfaces, items 7-12 not only resulted in unexpected long term performances in zero gas but also no lead oxide deposits under accelerated life testing. A Platinum coated electrode, item 7, gave the best long term performance in zero gas followed by Rhodium, item No. 12. It was observed that the condition of the surface of the substrate surface before plating greatly effected the test results in zero gas as to the number of hours the output readings stayed below 0.1% oxygen. To this end note that the identified "slightly rough surface" for the rhodium surface in item No. 11 was visible to the naked eye and produced inferior results to the rhodium surfaces described as smooth or smoothest. The degree of smoothness of the plated surface was graded on the basis of the zero gas tests so that the smoothest surface, item 9, produced the most acceptable test results as compared to item 10, the next smoothest surface. The condition of the plating bath also effected the results as can be observed from the results of a smooth surface for rhodium produced by a new production plating bath as compared to the other test results. Other than the smoothness observable by the unaided human eye, there does not appear to be a simple manner of defining the smoothness of the plated surface but the results speak for themselves.

The above establishes the dramatic difference in results between the cathode surfaces plated with rhodium and platinum in comparison to all of the remaining known metals tested. Although the platinum was superior to rhodium in the long term results, rhodium is presently the preferrable coating for a sensing electrode utilized and tested for the above described applications due to the difficulty in obtaining a source for plating platinum. Therefore, it has been found that a sensing electrode constructed of either of these two metals results in a gas sensor having a substantially longer operating life than present day gas sensing electrodes. No known gas sensing electrode for gas sensors utilized for the above described purposes takes advantage of the properties of either of these two metals.

A practical example of a gas sensing cathode electrode and gas analyzer for the above described applications is disclosed in the U.S. Pat. No. 3,767,552. The form of cathode electrode having a convex, apertured shape is disclosed in column 4, lines 4–24 of the patent.

We claim:

1. A sensor electrode for use in an electrochemical gas sensor for sensing the concentration of an electrochemically active gas in a gas mixture, said electrochemical gas sensor comprising a gas sensing cathode electrode constructed of an inert metal selected for rejecting lead species deposits thereon, and a metallic anode electrode immersed in a liquid electrolyte for sensing concentrations of electrochemically active gases in a gas mixture and wherein the selected electrolyte contains soluble species of the metal selected for the anode, the improvement comprising said sensing cathode electrode having a supporting substrate and a thin layer of Rhodium plated on the substrate to function as the gas sensing surface to which the electrochemically active gas is exposed whereby the sensing surface rejects the deposition of any soluble anode metal species thereon leading to an extended operative life for the rhodium sensing cathode electrode and thereby the electrochemical gas sensor.

2. A sensor electrode as defined in claim 1 wherein the metal for the anode is lead and the liquid electrolyte is an aqueous solution of potassium hydroxide, the electrochemical gas sensor is utilized for determining the oxygen concentration in a gas mixture exposed to said sensing cathode electrode, and said soluble species are lead oxide species, said rhodium gas sensing electrode rejects the deposition of the lead oxide species in the electrolyte.

3. A sensor electrode as defined in claim 1 wherein the electrochemical gas in the gas mixture includes carbon dioxide and no oxygen, the carbon dioxide is drawn into the electrolyte and thereby forms lead carbonate deposits whereby said rhodium plated gas sensing cathode is further characterized as rejecting the deposition of lead carbonate thereon for an extended time period.

4. A sensor electrode as defined in claim 1 wherein said improved gas sensing cathode electrode comprises an electrode substrate that is smooth, clean, and having no organic or inorganic inclusions thereon, and a thin layer of rhodium plated on said substrate having a preselected sensing area.

5. A sensor electrode for use in an electrochemical gas analyzer having a gas sensing cathode electrode constructed of an inert metal selected for rejecting lead species deposits thereon, and a metal anode electrode immersed in a liquid electrolyte for sensing concentrations of electrochemically active gases in a gas mixture including sensing the exhaust gases of a motor vehicle, wherein the electrolyte is further characterized as being of a strong basic nature, and said electrochemically active gases are exhaust gases containing carbon dioxide which is drawn into said electrolyte, when continuously exposed to carbon dioxide with no oxygen, for a preselected time, the improvement comprising said sensing cathode electrode having a supporting substrate and a thin layer of rhodium, plated on the substrate to function as the sensing surface to which said gas mixture is exposed.

6. A sensor electrode as defined in claim 5 wherein said gas analyzer anode metal is lead and the electrolyte is an aqueous solution of potassium hydroxide wherein the carbon dioxide is drawn into the electrolyte forming lead carbonate deposits that are rejected as deposits by said rhodium sensing surface leading to an extended long term performance of the sensing electrode and thereby said gas analyzer.

7. A sensor electrode for use in an electrochemical gas analyzer for detecting a preselected gas in a gas mixture when the electrode is used in an electrochemical gas sensing cell, the sensor electrode comprising an electrode substrate that is smooth, clean, and having no organic or inorganic inclusions thereon, and a thin layer of rhodium plated on said substrate having a preselected area resulting in a sensing electrode devoid of deposit sites that are capable of deposition thereon during the use of said sensing electrode in gas analysis that lead to the reduction in the useful life of said electrode.

8. A sensor electrode as defined in claim 7 wherein a thin layer of platinum is plated on said substrate that is characterized as being devoid of deposit sites.

9. A sensor electrode for use in an electrochemical gas sensor for sensing the concentration of an electrochemically active gas in a gas mixture, said gas sensor comprising a gas sensing cathode electrode constructed of an inert metal and a metallic anode electrode immersed in a liquid electrolyte for sensing concentrations of electrochemically active gases in a gas mixture and the selected electrolyte contains soluble species of the selected metal for the anode electrode, the improvement comprising a gas sensing cathode electrode having a supporting substrate and a thin layer of platinum deposited on the substrate to function as the gas sensing surface to which the electrochemically active gas is exposed whereby the platinum sensing surface rejects the deposition of any soluble anode metal species thereon leading to an extended operative life for the platinum gas sensing cathode electrode.

10. A sensor electrode as defined in claim 9 for a gas sensor is utilized for sensing the oxygen concentration in a gas mixture applied to said sensing cathode electrode wherein the metal selected for the anode electrode is lead and the liquid electrolyte is an aqueous solution of potassium hydroxide, and said soluble metal species are lead oxide species, said gas sensing electrode rejects the deposition of the lead oxide species in the electrolyte.

11. A sensor electrode as defined in claim 9 wherein said gas sensing cathode electrode comprises an electrode substrate that is smooth, clean, and having no organic or inorganic inclusions thereon, and a thin layer of platinum plated on said substrate having a preselected sensing area.

12. A sensor electrode for use in an electrochemical gas analyzer, said gas analyzer having a gas sensing cathode electrode constructed of an inert metal and a metallic anode electrode immersed in a liquid electrolyte for sensing concentrations of electrochemically active gases in a gas mixture including sensing the exhaust gases of a motor vehicle, the electrolyte being further characterized as being of a strong basic nature, and said exhaust gases containing carbon dioxide which is drawn into said electrolyte when continuously exposed to carbon dioxide with no oxygen for a preselected time, the improvement comprising said sensing cathode electrode for said gas analyzer having a supporting substrate and a thin layer of platinum plated on the substrate to function as the sensing surface.

13. A sensor electrode as defined in claim 12 wherein said anode metal is lead and the electrolyte is an aqueous solution of potassium hydroxide wherein the carbon dioxide is drawn into the electrolyte and forming lead carbonate deposits that are rejected by said platinum sensing suface.

* * * * *

UNITED STATES PATENT AND TRADEMARK OFFICE
CERTIFICATE OF CORRECTION

PATENT NO. : 5,714,046
DATED      : February 3, 1998
INVENTOR(S): Lauer et al

It is certified that error appears in the above-identified patent and that said Letters Patent is hereby corrected as shown below:

In the Claims:

Column 6:

Claims 9-13 now become claims 7-11; Claim 10 becomes Claim 8 and depends on Claim 7; Claim 11 becomes Claim 9 and depends on Claim 9 and depends on Claim 7; Claim 12 becomes Claim 10; Claim 12 becomes Claim 10; Claim 13 becomes Claim 11 and depends on Claim 10.

Signed and Sealed this

Eighth Day of September, 1998

Attest:

BRUCE LEHMAN

*Attesting Officer*    *Commissioner of Patents and Trademarks*